(12) United States Patent
Frauenkron et al.

(10) Patent No.: US 7,393,978 B2
(45) Date of Patent: Jul. 1, 2008

(54) METHOD FOR PRODUCING ETHYLENE-AMINES

(75) Inventors: Matthias Frauenkron, Freinsheim (DE); Thomas Krug, Worms (DE); Holger Evers, Mannheim (DE); Johann-Peter Melder, Böhl-Iggelheim (DE); Roderich Röttger, Mannheim (DE); Markus Siegert, Heidelberg (DE); Till Gerlach, Ludwigshafen (DE); Jan Nouwen, Brecht (BE); Ellen Dahlhoff, Limburgerhof (DE); Christian Miller, Ruppertsberg (DE)

(73) Assignee: BASF Aktiengesellschaft (DE)

( * ) Notice: Subject to any disclaimer, the term of this patent is extended or adjusted under 35 U.S.C. 154(b) by 52 days.

(21) Appl. No.: 10/566,419

(22) PCT Filed: Jul. 15, 2004

(86) PCT No.: PCT/EP2004/007861

§ 371 (c)(1),
(2), (4) Date: Aug. 7, 2006

(87) PCT Pub. No.: WO2005/012223

PCT Pub. Date: Feb. 10, 2005

(65) Prior Publication Data

US 2006/0276649 A1    Dec. 7, 2006

(30) Foreign Application Priority Data

Aug. 1, 2003   (DE) ................................ 103 36 003
Jun. 24, 2004  (DE) ...................... 10 2004 030 645

(51) Int. Cl.
C07C 209/60   (2006.01)
(52) U.S. Cl. ............... 564/469; 564/470; 564/511; 564/512; 544/358
(58) Field of Classification Search ............ None
See application file for complete search history.

(56) References Cited

U.S. PATENT DOCUMENTS

| 5,202,490 A | 4/1993 | Burgess et al. |
| 5,410,086 A | 4/1995 | Burgess |
| 2004/0220428 A1 | 11/2004 | Gerlach et al. |
| 2005/0016830 A1 | 1/2005 | Kaibel et al. |
| 2005/0070733 A1 | 3/2005 | Sigl et al. |

FOREIGN PATENT DOCUMENTS

| EP | 0 197 611 | 10/1986 |
| EP | 0 952 152 | 10/1999 |
| EP | 1 431 273 | 6/2004 |
| GB | 1 508 460 | 4/1978 |
| WO | WO-03/010125 | 2/2003 |
| WO | WO-03/047747 | 6/2003 |
| WO | WO-2005/014523 | 2/2005 |

OTHER PUBLICATIONS

Database CAPLUS on STN, Acc. No. 1968:467422, Boffa et al., IT 696938 (Oct. 21, 1995) (abstract).*

* cited by examiner

*Primary Examiner*—Brian J Davis

(57) ABSTRACT

Process for the preparation of ethylenamines, in particular diethylenetriamine (DETA), by continuous reaction of ethylenediamine (EDA) in the presence of a heterogeneous catalyst, where the reaction is carried out in a reaction column.

36 Claims, 2 Drawing Sheets

METHOD FOR PRODUCING ETHYLENE-AMINES

RELATED APPLICATIONS

This application is a national stage application (under 35 U.S.C. 371) of PCT/EP2004/007861 filed Jul. 15, 2004 which claims benefit of German application 103 36 003.4 filed Aug. 1, 2003 and German application 10 2004 030 645.1 filed Jun. 24, 2004.

The present invention relates to a process for the preparation of ethyleneamines, in particular diethylenetriamine (DETA), piperazine (PIP) and/or triethylenetetramine (TETA), by continuous reaction of ethylenediamine (EDA) in the presence of a heterogeneous catalyst.

Ethyleneamines are used as solvents, stabilizers, for the synthesis of chelating agents, synthetic resins, medicaments, inhibitors and interface-active substances.

In particular, diethylenetriamine (bis(2-aminoethyl)amine; DETA) is used as solvent for dyes and is a starting material for the preparation of ion exchangers, pesticides, antioxidants, corrosion inhibitors, complexing agents, textile auxiliaries and absorption agents for (acidic) gases.

The ethylenediamine ($H_2N-CH_2-CH_2-NH_2$; EDA) required as starting material can be prepared by known processes, for example by reaction of monoethanolamine (MEOA) with ammonia.

Numerous processes are described in the literature for the preparation of ethyleneamines.

According to the prior art, ethyleneamines such as DETA are prepared from monoethanolamine (MEOA) and ammonia mostly in fixed-bed reactors, where the catalysts comprise, as active component, for example nickel, cobalt, copper, noble metals such as Re, Ru, Rh, Pt, Pd, or combinations thereof. Support material may, for example, be $Al_2O_3$, $SiO_2$ or $ZrO_2$ or combinations of these and other oxides. To maintain the catalyst activity, it is in most cases necessary to introduce small amounts of hydrogen (e.g. about 0.001% by weight, based on the amount of feed).

The main product which arises in the process is EDA, and by-products which arise are DETA, piperazine (PIP) and higher ethyleneamines, i.e. ethyleneamines with a boiling point higher than DETA (at the same pressure), and other compounds, such as, for example, aminoethylethanolamine (AEEA).

Since DETA in particular is demanded on the market in relatively large amounts as well as the main product EDA, it is desirable to increase the selectivity of DETA compared to the selectivity obtained in a simple pass in the fixed-bed reactor. The selectivity of EDA and DETA can be controlled within certain limits by the molar ratio of ammonia to MEOA. A high ammonia excess favors the formation of EDA, particularly at a low MEOA conversion. At a low ammonia excess and a relatively large MEOA conversion, the selectivity of DETA, but also of the other by-products is increased.

It is also possible to return some of the EDA, following concentration of the reaction product, to the reactor, in order to increase the DETA selectivity. The formation of the other by-products, in particular AEEA, can, however, not thereby be avoided.

EP-A2-197 611 (Union Carbide Corp.) describes a process for the preparation of polyalkylenepolyamines by using two reactors connected in series.

In the first reactor, the amination of MEOA with ammonia takes place over transition metal catalysts (Ni, Re, support).

The reactor product is sent via a second reactor, which is likewise charged with a transition metal catalyst or with a phosphate catalyst. To control the product distribution and to increase the selectivity with respect to the linear ethyleneamines, ethylenediamine which originates from the work-up of the reaction product of the second reactor and also comprises MEOA and $H_2O$ is introduced before the second reactor.

A disadvantage of this process is that AEEA preferentially further reacts to give piperazine and not to give DETA, and additional amounts of AEEA are formed as a result of the reaction of EDA with MEOA.

The synthesis of DETA can take place by known methods also by reacting EDA in a fixed-bed reactor, where the by-product produced is mainly PIP (cf. e.g. U.S. Pat. No. 5,410,086 (Burgess), GB-A-1,508,460 (BASF AG) and WO-A1-03/010125 (Akzo Nobel)).

At a conversion of, for example, about 30%, a DETA selectivity of about 70% can be achieved. If pure EDA is used as starting material, no AEEA is formed as by-product. The formation of higher ethyleneamines is largely avoided by the partial conversion procedure.

Due to the unfavorable position of the chemical equilibria, however, more PIP would be formed at a higher conversion. Furthermore, due to the formation of ammonia during the conversion of EDA to DETA (2 EDA→DETA+$NH_3$), the back reaction of DETA with ammonia to give EDA is also increasingly gaining in importance.

The partial conversion procedure leads to high circulation streams of EDA (recycle) and thus to increased energy consumption, particularly in the EDA purification column.

BASF's German patent application No. 10335991.5 of Aug. 1, 2003 relates to a process for the preparation of ethyleneamines by reacting monoethanolamine (MEOA) with ammonia in the presence of a catalyst in a reactor (1) and separating the resulting reaction product, where ethylenediamine (EDA) obtained during the separation is reacted in a separate reactor (2) in the presence of a catalyst to give diethylenetriamine (DETA), and the resulting reaction product is passed to the separation of the reaction product resulting from reactor 1.

For the addition of alcohols onto olefins to give corresponding ethers [e.g. MTBE (methyltertiary-butyl ether) and TAME (tertiary-amyl methyl ether)] there are processes known in the literature which are carried out in a reaction column. The processes, also referred to as reactive distillation, are described in detail, for example, in the textbook "Reactive Distillation", edited by K. Sundmacher and A. Kienle, Verlag Wiley-VCH (2003).

Applications of reactive distillation also exist in the fields of esterifications, saponifications and transesterifications, preparation and saponification of acetals, preparation of alkoxylates, aldol condensations, alkylations, hydrolysis of epoxides, hydration of olefins, isomerizations and hydrogenations.

It is an object of the present invention to find an improved economical process for the selective preparation of ethyleneamines, including, in particular, diethylenetriamine (DETA), in high yield and space-time yield (STY).

[Space-time yields are given in 'product quantity/(catalyst volume·time)' ($kg/(I_{cat.} \cdot h)$) and/or 'product quantity/(reactor volume·time)' ($kg/(I_{reactor} \cdot h)$].

We have found that this object is achieved by a process for the preparation of ethyleneamines by continuous reaction of ethylenediamine (EDA) in the presence of a heterogeneous catalyst, which comprises carrying out the reaction in a reaction column.

The ethyleneamines are, in particular, diethylenetriamine (DETA), piperazine (PIP) and/or triethylenetetramine (TETA).

The reaction proceeds, then, for example, in accordance with the following equations:

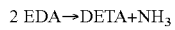

2 EDA→DETA+NH$_3$

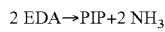

2 EDA→PIP+2 NH$_3$

3 EDA→TETA+2 NH$_3$

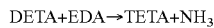

DETA+EDA→TETA+NH$_3$

DETAILED DESCRIPTION

Figure 1:
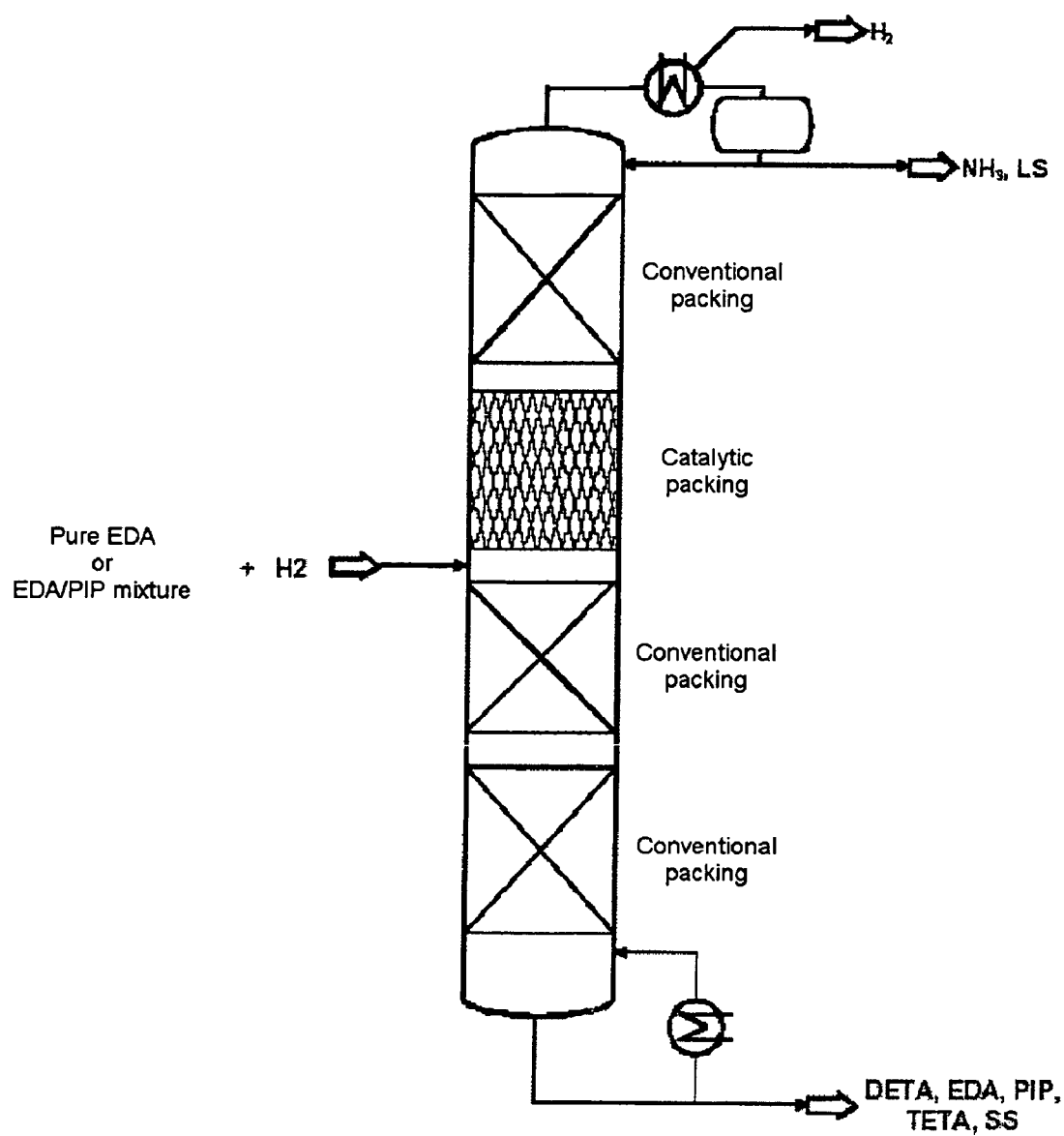
FIGS. 1-2 schematically illustrate columns which are practices of the invention.

According to the invention, it has been recognized that the disadvantages of the processes of the prior art are avoided when the synthesis of ethyleneamines, in particular DETA, is carried out by continually reacting EDA in a reaction column (reactive distillation). The continuous stripping of DETA and/or TETA from the column below the reaction zone (via the bottom and/or via a side take-off) can largely suppress secondary reactions and thereby permit a procedure with a high conversion and even complete conversion of EDA.

By continuously removing ammonia from the column (preferably at the top of the column, also as a mixture with components with lower boiling points than DETA), the back reaction of DETA to EDA is largely suppressed, thus accelerating the formation of DETA. The reaction can thus be carried out at other pressures, advantageously lower pressures, than in the optimum pressure range when using a conventional fixed-bed reactor (tubular reactor with catalyst fixed bed).

The absolute pressure in the column is preferably in the range from >0 to 20 bar, for example in the range from 1 to 20 bar, in particular 5 to 10 bar.

The temperature in the section of the column in which the reaction of EDA to ethyleneamines takes place (reaction zone) is preferably in the range from 100 to 200° C., in particular 140 to 160° C.

The number of theoretical plates in the column is preferably in the range from 5 to 100 in total, more preferably 10 to 20.

The number of theoretical plates in the reaction zone is preferably in the range from 1 to 30, in particular 1 to 20, in particular 1 to 10, for example 5 to 10.

The number of theoretical plates in the enriching section above the reaction zone is preferably in the range from 0 to 30, in particular 1 to 30, more particularly 1 to 15, in particular 1 to 5.

The number of theoretical plates in the stripping section below the reaction zone is preferably in the range from 0 to 40, particularly 5 to 30, in particular 10 to 20.

The addition of EDA to the column can take place below the reaction zone in liquid form or in gaseous form.

The addition of EDA to the column can also take place in liquid form above the reaction zone.

In the process according to the invention, both pure EDA, e.g. in a purity of >98% by weight, in particular >99% by weight, and also EDA which comprises piperazine (PIP), e.g. >0 to 25% by weight of PIP, and/or other ethyleneamines, can be fed into the column.

It is also possible to use the EDA crude product from a reaction of MEOA with ammonia following partial or complete removal of ammonia and water.

The reaction is particularly preferably carried out in the presence of hydrogen, in particular in the presence of from 0.0001 to 1% by weight, preferably 0.001 to 0.01% by weight, of hydrogen, based on the feed amount of EDA.

The addition of hydrogen to the column preferably takes place below the reaction zone.

A mixture of ammonia, other components with a boiling point lower than DETA (at the same pressure) (low-boiling components) and optionally hydrogen is preferably removed via the top of the column.

The mixture removed via the top of the column can also comprise partial amounts of unreacted EDA.

The mixture removed overhead can also be partially condensed and, during this, ammonia and optionally hydrogen are removed predominantly in gaseous form (evaporated off) and the liquefied fraction can be fed to the column as reflux.

The weight ratio of the amount of reflux of the column (column reflux amount) to the amount of feed to the column is here preferably in the range from 0.1 to 30, particularly preferably 0.5 to 10, in particular 0.5 to 2.

A mixture of DETA, piperazine (PIP), TETA and other components with a boiling point higher than that of DETA (at the same pressure) (high-boiling components) is preferably removed via the bottom of the column.

The mixture removed via the bottom of the column may also comprise partial amounts of unreacted EDA or the total amount of unreacted EDA.

In one particular embodiment, the column below the reaction zone is subdivided by a side take-off.

Unreacted EDA, PIP or mixtures thereof are preferably removed via the side take-off.

The product removed via the side take-off may also comprise DETA.

The product produced via the side take-off is removed in liquid form or in gaseous form.

In the reaction zone, the catalyst used is preferably a catalyst comprising Ni, Co, Cu, Ru, Re, Rh, Pd and/or Pt or a shape-selective zeolite catalyst or a phosphate catalyst.

The metal or metals of the transition metal catalyst, which preferably include Ru, Re, Rh, Pd and/or Pt, have preferably been applied to an oxidic support material (e.g. Al$_2$O$_3$, TiO$_2$, ZrO$_2$, SiO$_2$) or to a zeolite or active carbon support material.

In a preferred embodiment, the catalyst used in the reaction zone is a catalyst comprising Pd and zirconium dioxide support material.

The total metal content of the supported transition metal catalysts is preferably in the range from >0% to 80% by weight, particularly 0.1% to 70% by weight, more particularly 5% to 60% by weight, more particularly 10% to 50% by weight, all percentages being based on the weight of the support material.

In the case of supported noble metal catalysts, which are preferred, the total noble metal content is in particular in the range from >0% to 20% by weight, particularly 0.1% to 10% by weight, very particularly 0.2% to 5% by weight, more particularly 0.3% to 2% by weight, all percentages being based on the weight of the support material.

The heterogeneous catalysts can be accommodated in the form of fixed catalyst beds within the column or in separate containers outside the column. They can also be used as loose beds, e.g. as a loose bed in a distillation packing, be shaped to give dumped packings or moldings, for example pressed to give Raschig rings, incorporated into filter fabric and shaped to give bales or column packings, applied to distillation packings (coating) or be used in the form of a suspension in the column, here preferably in the form of a suspension on column trays.

In processes with heterogeneously catalyzed reactive distillations, the bales technology developed by CDTech can advantageously be used.

Further technologies are special tray constructions with packed or suspended catalysts.

Multichannel packings or cross channel packings (see e.g. WO-A-03/047747) permit simple insertion and removal of catalysts which are in particulate form (e.g. spheres, pellets, tablets) with low mechanical stress of the catalyst.

An important point for reactive distillation is the provision of the residence time required for the course of the reaction. It is necessary to increase the residence time of the liquid in the column in a targeted manner compared with a nonreactive distillation. Special designs of column internals, for example tray columns with bubblecap trays with considerably increased fill level, high residence times in the downcomers of tray columns and/or also separately arranged external delay-time containers are used. Obstructive packings offer the possibility of increasing the residence time of the liquid by approximately a factor of 3 compared with columns packed with dumped or arranged packing.

The design of the reaction column (number of plates in the column sections enriching section, stripping section and reaction zone, reflux ratio, etc.) can be undertaken by the person skilled in the art in accordance with methods with which he is familiar.

Reaction columns are described, for example, in the literature in:

"Reactive distillation of nonideal multicomponent mixtures", U. Hoffmann, K. Sundmacher, March 1994; Trondheim/Norway, "Prozesse der Reaktivdestillation" [Processes of reactive distillation], J. Stichlmair, T. Frey, Chem. Ing. Tech. 70 (1998) 12, pages 1507-1516, "Thermodynamische Grundlagen der Reaktivdestillation" [Thermodynamic principles of reactive distillation], T. Frey, J. Stichlmair, Chem. Ing. Tech. 70 (1998) 11, pages 1373-1381, WO-A-97/16243 dated May 9, 1997, DD-Patent 100701 dated Oct. 5, 1973, U.S. Pat. No. 4,267,396 dated May 12, 1981, "Reaktionen in Destillationskolonnen" [Reactions in distillation columns], G. Kaibel, H.-H. Mayer, B. Seid, Chem. Ing. Tech. 50 (1978) 8, pages 586-592, and literature cited therein, DE-C2-27 14 590 dated Aug. 16, 1984, EP-B-40724 dated May 25, 1983, EP-B-40723 dated Jul. 6, 1983, DE-C1-37 01 268 dated Apr. 14, 1988, DE-C1-34 13 212 dated Sep. 12, 1985, "Production of potassium tert-butoxide by azeotropic reaction distillation", Wang Huachun, Petrochem. Eng. 26 (1997) 11, "Design aspects for reactive distillation", J. Fair, Chem. Eng. 10 (1998), pages 158-162, EP-B1-461 855 dated Aug. 9, 1995, "Consider reactive distillation", J. DeGarmo, V. Parulekar, V. Pinjala, Chem. Eng. Prog. 3 (1992), EP-B1-402 019 dated Jun. 28, 1995, "La distillation réaktive", P. Mikitenko, Pétrole et Techniques 329 (1986), pages 34-38, "Geometry and efficiency of reactive distillation bale packing", H. Subawalla, J. González, A. Seibert, J. Fair, Ind. Eng. Chem. Res. 36 (1997), pages 3821-3832, "La distillation réactive", D. Cieutat, Pétrole et Techniques 350 (1989), "Preparation of tert-amyl alcohol in a reactive distillation column", J. González, H. Subawalla, J. Fair, Ind. Eng. Chem. Res. 36 (1997), pages 3845-3853, "More uses for catalytic distillation", G. Podrebarac, G. Rempel, Chem. Tech. 5 (1997), pages 37-45, "Advances in process technology through catalytic distillation", G. Gildert, K. Rock, T. McGuirk, CDTech, pages 103-113, WO-A1-03/047747 dated Jun. 12, 2003 (BASF AG), and

WO-A1-97/35834.

In a preferred embodiment, the process of the present invention is carried out as described in WO-A1-03/047747 in a column for carrying out reactive distillations in the presence of a heterogeneous particulate catalyst having an ordered packing or random packings which form intermediate spaces in the column interior, wherein the column has first and second part regions which are arranged in alternation and which differ by the specific surface area of the ordered packing or random packings in such a manner that in the first part regions the quotient of hydraulic diameter for the gas stream through the ordered packing or random packings and equivalent diameter of the catalyst particles is in the range from 2 to 20, preferably in the range from 5 to 10, with the catalyst particles being introduced into the intermediate spaces, distributed and discharged loose under the action of gravity and in the second part regions the quotient of the hydraulic diameter for the gas stream through the ordered packing or random packings and equivalent diameter of the catalyst particles is less than 1 and no catalyst particles are introduced into the second part regions. Preferably the column is operated with respect to its gas and/or liquid loadings in such a manner that a maximum of from 50% to 95% and preferably from 70% to 80% of the flooding limit loading is reached. Cf. loc. cit., claims 9 and 10.

The work-up of the product streams produced in the process according to the invention, which primarily comprise the particularly desired DETA, but also triethylenetriamine (TETA), PIP and unreacted EDA, can take place in accordance with the distillation process known to the person skilled in the art. (compare e.g. PEP Report No. 138, "Alkyl Amines", SRI International, 03/1981, pages 81-99, 117).

The distillation columns required for the distillative isolation of the individual pure products, primarily of the particularly desired DETA, can be designed by the person skilled in the art using methods with which he is familiar (e.g. number of plates, reflux ratio, etc.).

The procedure with a side take-off in the stripping section below the reaction zone of the reaction column offers particular advantages during the further work-up for isolating the individual pure products.

The side take-off steam, consisting primarily of PIP, unreacted EDA or mixtures thereof, comprises only small amounts of DETA and high-boiling components, in particular in the case of the gaseous removal of the side take-off stream. It can therefore be fed directly within the work-up section, separately from the bottom take-off stream of the reaction column, to the place where the purification of EDA and PIP is carried out, instead of firstly passing through the removal of the low-boiling components from DETA and high-boiling components.

Partial amounts of the side stream can also be returned to the reaction column itself. This is particularly advantageous when the side stream comprises primarily EDA and little or no PIP.

The bottom take-off stream of the reaction column in this procedure comprises fewer low-boiling components (EDA and PIP), thus relieving the pressure on the column for removing the low-boiling components from DETA and high-boiling components.

If the reactive distillation is carried out at low pressures, for example 1 to 3 bar, it is also possible to obtain the bottom take-off stream at bottom temperatures of from about 200 to 240° C. free from EDA and PIP. The bottom take-off stream can then optionally be passed to the work-up section at the place where the purification of DETA is carried out, instead of firstly passing through the separation of the low-boiling components from DETA and high-boiling components.

The process of the present invention makes it possible to produce DETA at a selectivity of >18%, especially >20% and more particularly >22%, all percentages being based on EDA, coupled with an EDA conversion of >30%, especially >40% and more particularly >50%.

EXAMPLES

Example A

FIG. 1 in Annex 1 shows a version of the process according to the invention in which pure EDA or an EDA/PIP mixture is fed, together with hydrogen, to the reaction column continuously below the catalytic packing, and a mixture comprising DETA, unreacted EDA, PIP, TETA and high-boiling components (SS, i.e. components with a boiling point higher than DETA) is obtained via the bottom. Ammonia, hydrogen and low-boiling components (LS, i.e. components with a boiling point lower than DETA) are separated off overhead.

Example B

Figure 2:
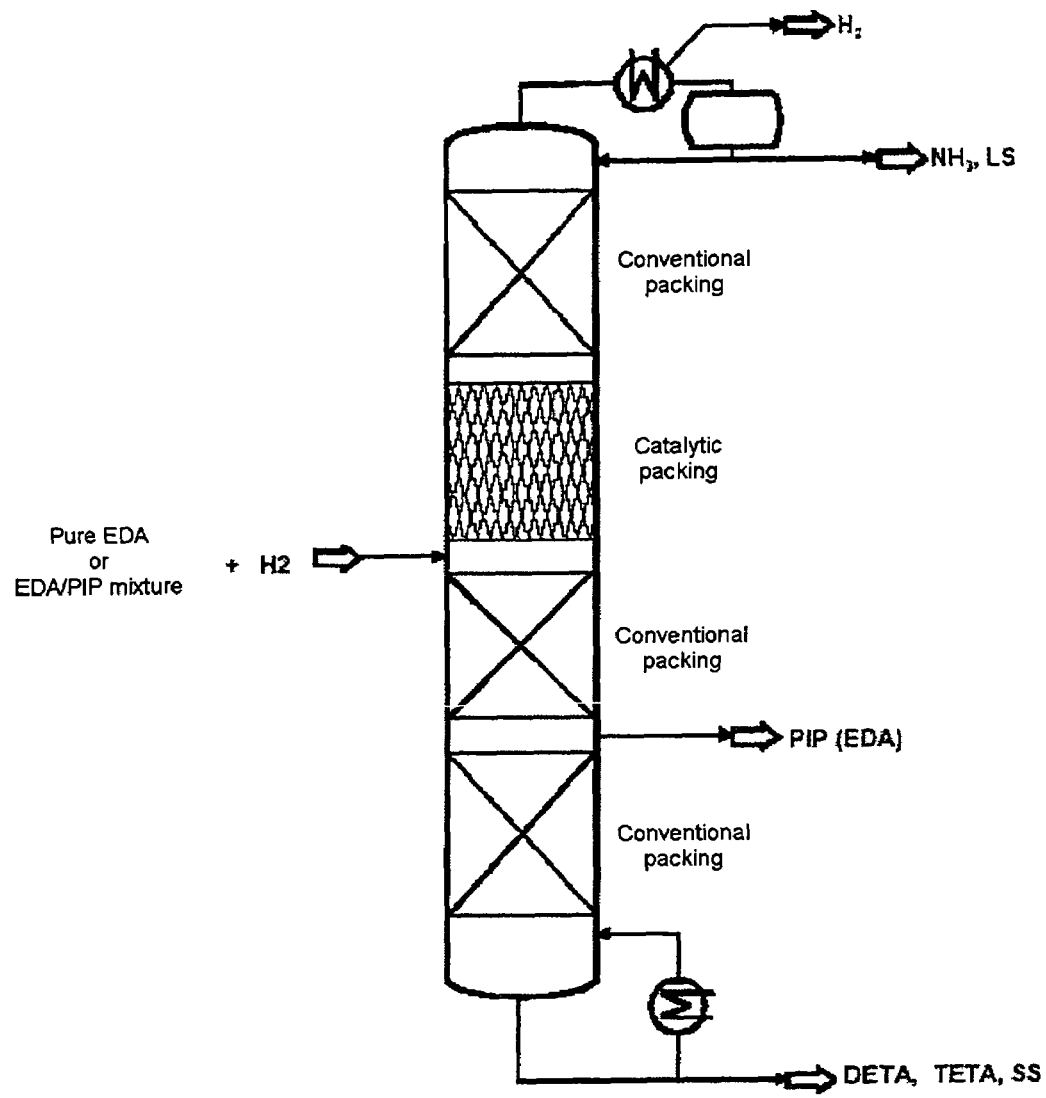

FIG. 2 in Annex 2 shows a version of the process according to the invention in which pure EDA or an EDA/PIP mixture, together with hydrogen, is passed to the reaction column continuously below the catalytic packing, and a mixture comprising DETA, TETA and high-boiling components (SS, i.e. components with a boiling point higher than DETA) is obtained via the bottom. Ammonia, hydrogen and low-boiling components (LS, i.e. components with a boiling point lower than DETA) are removed overhead.

In a side take-off in the stripping section below the reaction zone of the reaction column, PIP, optionally as a mixture with EDA, is separated off.

Examples 1 to 3

The catalyst was prepared using zirconium dioxide extrudates 3.2 mm in diameter and 1-2 cm in length.

2700 g of the support were drenched with 770.0 ml (=92% of $H_2O$ uptake) of an aqueous palladium nitrate solution, resulting in a calculated palladium loading of 0.9% by weight of palladium. The drenching was carried out repeatedly. This was followed by drying in a drying cabinet at 120° C. (heating to 120° C. took 1 h) for 6 h and calcination in a muffle furnace at 450° C. (heating to 450° C. took 2 h) for 2 h.

The reactions of examples 1 to 4 were all carried out at an absolute pressure of 5 bar. Hydrogen was fed into the column at below the catalytic layer at a rate of 6 l/h.

Examples 1 and 2 were carried out after 755 g of the prepared catalyst had been filled into a 55 mm diameter laboratory column containing an ordered packing as recited in claim 9 of patent application WO-A1-03//047747 and the related description. The number of theoretical plates below the catalyst bed was 6. The catalytic packing had 3.5 theoretical plates. The number of theoretical plates above the catalyst bed was 1.

Example 1

Liquid EDA was supplied at room temperature above the catalytic layer at a rate of 400 g/h. Reflux was set to 800 g/h. The base of column temperature in steady-state operation was 186° C.

The bottom product of the column had a composition (in % by weight) of 65% EDA, 9.7% DETA and 16% piperazine. The other components were high boilers. This amounted to a DETA selectivity of 25% coupled with an EDA conversion of 41%.

Example 2

Liquid EDA was supplied at room temperature below the catalytic layer at a rate of 400 g/h. Reflux was set to 400 g/h. The base of column temperature in steady-state operation was 183° C.

The bottom product of the column had a composition (in % by weight) of 74.6% EDA, 6.1% DETA and 13.2% piperazine. The other components were high boilers. This amounted to a DETA selectivity of 21.7% coupled with an EDA conversion of 30.6%.

Example 3 was carried out after 934 g of the prepared catalyst had been filled into a 55 mm diameter laboratory column containing an ordered packing as recited in claim 9 of patent application WO-A1-03//047747 and the related description.

The number of theoretical plates below the catalyst bed was 15. The catalytic packing had 10 theoretical plates. The number of theoretical plates above the catalyst bed was 10.

Example 3

Liquid EDA was supplied at room temperature above the catalytic layer at a rate of 100 g/h. Reflux was set to 800 g/h. The base of column temperature in steady-state operation was 162° C.

The bottom product of the column had a composition (in % by weight) of 55% EDA, 12% DETA and 21% piperazine. The other components were high boilers. This amounted to a DETA selectivity of 21% coupled with an EDA conversion of 55%.

We claim:

1. A process for the preparation of ethyleneamines by continuous reaction of ethylenediamine (EDA) in the presence of a heterogeneous catalyst, which comprises carrying out the reaction in a reaction column by means of reactive distillation.

2. The process for the preparation of ethyleneamines according to claim 1, where the ethyleneamines are diethylenetriamine (DETA), piperazine (PIP), and/or triethylenetetramine (TETA).

3. The process according to claim 1, wherein the absolute pressure in the column is in the range from >0 to 20 bar.

4. The process according to claim 1, wherein the temperature in the section of the column in which the reaction of EDA to ethyleneamines takes place (reaction zone) is in the range from 100 to 200° C.

5. The process according to claim 1, wherein the number of theoretical plates in the column is in the range from 5 to 100 in total.

6. The process according to claim 1, wherein the number of theoretical plates in the reaction zone is in the range from 1 to 30.

7. The process according to claim 1, wherein the number of theoretical plates in the enriching section above the reaction zone is in the range from 0 to 30.

8. The process according to claim 1, wherein the number of theoretical plates in the stripping section below the reaction zone is in the range from 0 to 40.

9. The process according to claim 1, wherein the catalyst used in the reaction zone is a catalyst comprising Ni, Co, Cu, Ru, Re, Rh, Pd and/or Pt or a shape-selective zeolite catalyst or a phosphate catalyst.

10. The process according to claim 1, wherein the catalyst used in the reaction zone is a catalyst comprising Pd and zirconium dioxide support material.

11. The process according to claim 1, wherein the catalyst is introduced into the reaction column in the form of a loose bed.

12. The process according to claim 1, wherein the catalyst is introduced into a distillation packing in the form of a loose bed.

13. The process according to claim 1, wherein the catalyst is in the form of a coating on a distillation packing.

14. The process according to claim 1, wherein the catalyst is in a retention container situated above the column.

15. The process according to claim 1, wherein the addition of EDA to the column takes place in liquid from below the reaction zone.

16. The process according to claim 1, wherein the addition of EDA to the column takes place in a gaseous form below the reaction zone.

17. The process according to claim 1, wherein the addition of EDA to the column takes place in liquid form above the reaction zone.

18. The process according to claim 1, wherein EDA is passed to the column in a purity of >98% by weight.

19. The process according to claim 1, wherein EDA, piperzine (PIP) and/or other ethyleneamines are introduced into the column.

20. The process according to claim 1, wherein the reaction is carried out in the presence of hydrogen.

21. The process according to claim 20, wherein the reaction is carried out in the presence of from 0.0001 to 1% by weight of hydrogen, based on the feed amount of EDA.

22. The process according to claim 20, wherein the addition of hydrogen to the column takes place below the reaction zone.

23. The process according to claim 1, wherein a mixture of ammonia and other components with a boiling point lower than DETA (low-boiling components) is removed via the top of the column.

24. The process according to claim 23, wherein the mixture removed from the top of the column also comprises partial amounts of unreacted EDA.

25. The process according to claim 23, wherein the mixture removed overhead is partially condensed, and during this ammonia is removed wherein the ammonia is in a form which is more gaseous than non-gaseous, and the liquefied fraction is fed to the column as reflux.

26. The process according to claim 1, wherein the weight ratio of the amount of reflux in the column to the amount of feed to the column is in the range from 0.1 to 30.

27. The process according to claim 1, wherein a mixture of DETA, piperzine (PIP), TETA and other components with a boiling point higher than DETA (high-boiling components) is removed by the bottom of the column.

28. The process according to claim 27, wherein the mixture removed by the bottom of the column also comprises partial amounts of unreacted EDA or the total amount of unreacted EDA.

29. The process according to claim 1, wherein the column below the reaction zone is divided by a side-take off.

30. The process according to claim 29, wherein unreacted EDA, PIP or mixtures thereof are removed via the side take-off.

31. The process according to claim 29, wherein product removed via the side take-off comprises DETA.

32. The process according to claim 29, wherein product produced via the side take-off is removed in liquid form.

33. The process according to claim 29, wherein product produced via the side take-off is removed in gaseous form.

34. The process according to claim 1 for producing DETA at a selectivity of >20%, based on EDA, coupled with an EDA conversion of >30%.

35. The process according to claim 23, wherein hydrogen is removed with the ammonia.

36. The process according to claim 25, wherein hydrogen is removed with the ammonia.

\* \* \* \* \*